United States Patent [19]

DeLong

[11] Patent Number: 4,990,038
[45] Date of Patent: Feb. 5, 1991

[54] ROTATIONALLY AND AXIALLY RESTRAINED DRILL BIT AND CHUCK ASSEMBLY

[75] Inventor: Robert DeLong, Temple City, Calif. 91780

[73] Assignee: G & H Technology, Inc., Camarillo, Calif.

[21] Appl. No.: 471,624

[22] Filed: Jan. 29, 1990

[51] Int. Cl.⁵ .............................................. B23B 47/00
[52] U.S. Cl. .................................. 408/127; 408/226; 408/240
[58] Field of Search .................... 408/127, 226, 239 R, 408/240; 279/42, 48, 50; 433/127, 128, 165

[56] References Cited

U.S. PATENT DOCUMENTS

| | | | |
|---|---|---|---|
| 256,050 | 4/1882 | Richmond | 433/128 |
| 556,182 | 3/1896 | Grady | 408/127 |
| 2,025,779 | 12/1935 | Roelke | 279/48 |
| 2,188,426 | 1/1940 | Blair | 279/42 |
| 2,773,693 | 12/1956 | Chittenden | 279/48 |

FOREIGN PATENT DOCUMENTS

| | | | |
|---|---|---|---|
| 2918816 | 12/1979 | Fed. Rep. of Germany | 433/128 |
| 253166 | 2/1948 | Switzerland | 433/128 |
| 501072 | 2/1939 | United Kingdom | 408/127 |

*Primary Examiner*—Daniel W. Howell
*Attorney, Agent, or Firm*—George J. Netter

[57] ABSTRACT

A drill bit and chuck for interconnection with the end of a flexible drive shaft which axially and rotationally restrains the drill bit against becoming separated from the chuck during an operation requiring bone drilling, for example. The drill bit drive end has an eccentrically mounted boss with an enlarged head. A collet has an internal wall with an eccentric opening for receiving and locking with the drill bit boss head. The opposite end of the collet is staked onto the flexible shaft.

7 Claims, 1 Drawing Sheet

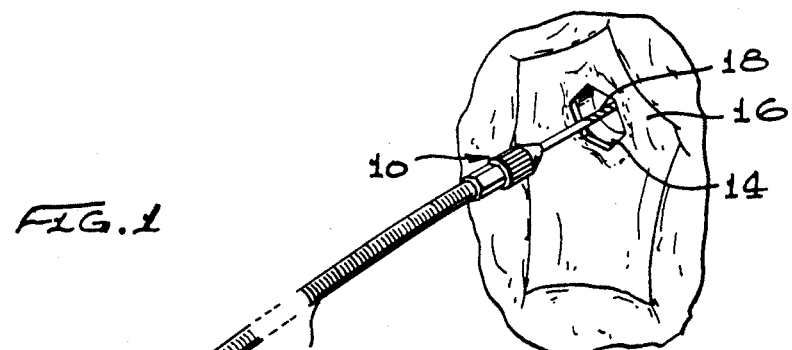
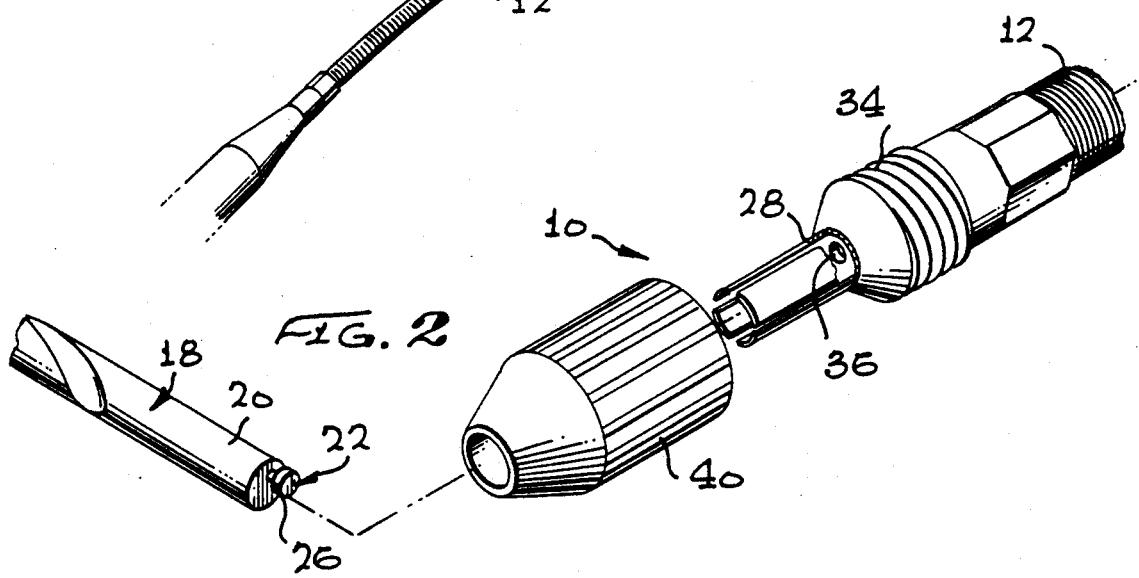
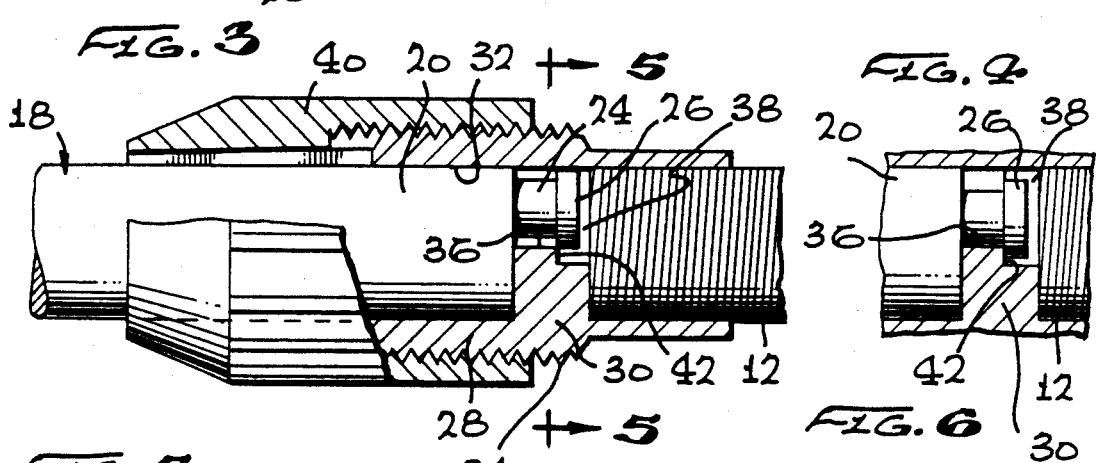
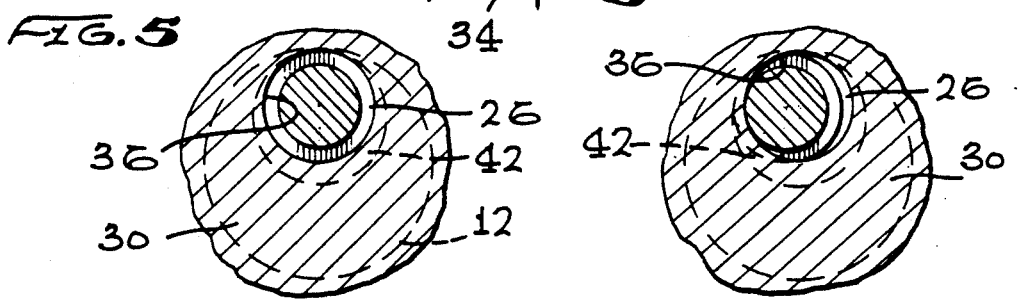

ROTATIONALLY AND AXIALLY RESTRAINED DRILL BIT AND CHUCK ASSEMBLY

BACKGROUND OF THE INVENTION

1. Field of the Invention

The present invention relates generally to a drill and drill chuck assembly for connection with a flexible drive shaft, and, more particularly, to such a drill and chuck assembly especially adapted for use in medical implant drilling, (e.g. drilling into shoulder or hip bones) to provide axial and rotational restraint for the drill as well as providing a construction which is readily disassembled for sterilization of its parts.

2. Description of Related Art

In a number of different medical implant operations, an important step is the drilling of holes into bones for receiving screws to secure implanted sockets, and the like. In this context, it is important, due to the operation environment, that a drill bit and its motor drive be interconnected by a flexible member so that the surgeon can drill holes in a hip or shoulder bone, for example, at various angles. It is not unusual, because of restricted access, that the surgeon must drill at 90 degrees or more relative to the drill motor. Also, as a final step in the drilling process, the drill is reversed in direction and pulled out of the bone. Of course, it is highly important that the drill not become disengaged from the flexible shaft chuck since this could require surgical removal which could become complicated. Clearly, it is highly desirable that the drill cannot become inadvertently disengaged from the flexible shaft by either axially applied force or rotational torquing.

One approach in the past has been to weld or braze the drill directly to the flex shaft. However, in this case when the drill gets dull it is then necessary that the entire device be replaced which, of course, is costly.

In another known apparatus, a cross pin is brazed onto the drill bit shank and a mating notch is formed on the chuck collet. The drill is installed with the cross pin engaged into the mating notch and a sleeve threaded over the two parts to retain the cross pin. Disadvantages of this apparatus are that the drill shank has to be cross drilled and of course the pin brazed in place with close centering on the cross pin. The medical community does not find this completely satisfactory in that it particularly requires completely removing the sleeve to replace the drill bit.

In a still further known approach, a quick disconnect type of assembly has clocking teeth, and a multiplicity of parts that do not readily disassemble for sterilization.

In yet another known device, a threaded hole on the end of a fitting for the flexible shaft mates with a thread on the end of the drill shank. This device has the undesirable disadvantage in that the drill could disengage from the flexible shaft thereby leaving the drill bit in the patient and disassembly of the drill bit cannot be achieved by hand and may require extra tools.

SUMMARY OF THE INVENTION

It is a primary aim and object of the present invention to provide a drill and chuck assembly for use with a flexible drive shaft which prevents individual rotation of the drill in a reverse direction.

Another object of the invention is to provide a drill and chuck assembly, as in the previous object, which has axial restraint preventing the drill from being removed by the mere application of an axial force.

Yet another object of the invention is provision of a drill and chuck assembly which is readily disassembled for sterilization of its various parts.

The drill bit contains on its drive end surface, a boss having an enlarged cylindrical head secured to the drill end by a smaller diameter stem. The stem interconnects the drill bit end at a point eccentrically located from the drill bit cylindrical axis.

A slotted cylindrical collet has an outer threaded end, for receipt on a similarly threaded sleeve whose mating taper clamps the tapered portion of the collet. The opposite end of the collet includes an inner chamber to engage with the flexible drive shaft and is ultimately staked for retention. The collet internal bottom wall includes a first opening located off the collet opening centerline and transverse dimensions slightly larger than that of the enlarged drill boss head. In addition, the relatively small collet opening in the bottom wall enlarges out into a larger chamber which interconnects with the smaller opening via a shoulder.

In use, the drill bit is placed within the collet such that the boss passes through the small opening and with the oversized boss head positioned within the bottom wall chamber. The drill bit is then rotated slightly either way which locks the enlarged head onto the shoulder in the bottom wall. A threaded sleeve is then secured over the collet which clampingly secures the drill bit by radial force exerted onto the slotted tapered collet.

With the boss enlarged head locked behind the shoulder, the drill cannot be removed from the collet by the mere application of an axial force. In the event the sleeve should become loosened allowing the drill to rotate, all it would do is move the enlarged head a limited amount to another part of the shoulder or stay put depending on initial position and still be retained against further rotation as well as being restrained from axial removal from the collet.

When it is desired to remove the drill from the flexible shaft, the sleeve is loosened and the drill may b readily twisted by hand in order to align the drill bit oversized boss head with the small opening in the collet bottom wall and then axially withdrawing the drill bit from the collet.

DESCRIPTION OF THE DRAWING

In the accompanying drawing:

FIG. 1 is a perspective view showing the present invention being used during a medical implant operation;

FIG. 2 shows the drill bit and chuck of the present invention with its various parts in exploded relation;

FIG. 3 is a side elevational, sectional view of the invention showing the drill bit being inserted into the chuck;

FIG. 4 is a detailed sectional view showing the drill bit boss in locking relation to the chuck collet;

FIG. 5 is an end elevational sectional view taken along the line 5—5 of FIG. 3; and FIG. 6 is an end elevational view similar to FIG. 5 showing the drill boss locked within the chuck collet.

DESCRIPTION OF A PREFERRED EMBODIMENT

Turning now to the drawings and particularly FI6. 1, the chuck and drill bit assembly of the present invention, enumerated generally as 10, is shown mounted onto the end of a flexible drive cable 12 for use in a medical implant operation. More particularly, it is a frequent requirement during implant operations to drill holes in one or more locations (e.g., shoulder, hip) which is typically accomplished by locating the predrilled implant socket as a template 14 over the bone area 16 and drilling at positions identified by template openings. Frequently, because of restricted access to the operation site, the actual drilling is performed at 90 or more degrees to the drill motor rotational shaft axis, and, therefore, the flexible shaft 12 is necessary.

On completion of the drilling, the drill is reversed and backed out of the opening. It is highly desirable that the drill not come loose from the chuck either during drilling or during the withdrawal process since it might then require additional surgical techniques to remove the drill from the bone which would be highly undesirable.

A drill bit 18 which is most advantageously employed in the assembly 10 includes a conventional shank portion 20. The drive end of the drill bit has a boss 22 consisting of a relatively small diameter stem 24 secured to the drill drive end (e.g., integrally machined) which terminates in a larger diameter head 26. The stem is secured to the drill end eccentrically of the drill central axis, but not so that the head 26 peripheral edge extends beyond the shank surface.

A collet 28 consists of a hollow, tapered cylindrical metal part having an interior wall 30 dividing the bore into substantially two parts. A first part 32 has an interior diameter such as to enable sliding receipt of the drill bit therewithin, the outer surface of this same part being threaded at 34. The opposite end of the collet is internally dimensioned to receive the end of the flexible shaft 12 and staked together.

The collet internal wall 30 has an opening 36 formed therein eccentrically of the opening centerline axis and of such diameter as to enable sliding receipt of the boss head 26 therein when the drive end of the drill bit is located within the collet. The wall 30 has a thickness adjacent the opening 36 that is less than the stem length which then opens up into a chamber 38 having cross-sectional dimensions greater than the diameter of the boss head 26. Accordingly, when the drill bit is correctly positioned within the collet the boss head can pass through the opening and be located within the chamber 38.

A shoulder 42 is provided on that side of the wall 30 facing the end of the flexible shaft 12 and extends toward the shaft end a sufficient amount to prevent contact between the shaft end and the boss head 26 (FIG. 3) when assembled.

A cylindrical sleeve 40 has a threaded bore which can be received onto the collet threads 34 and on advancing clamps the collet about the drill bit 18.

To assemble a drill bit 18 into the collet 28, first the sleeve 40 must be loosened. Then the drill bit drive end is slid into the collet first part 32 and radially manipulated until the boss head 26 passes through the collet central wall opening 36 (FIG. 5), after which the drill bit is rotated until the head 26 is locked behind the wall 30 as shown in FIG. 6. When locked in this manner, the drill bit cannot be removed by mere application of an axial withdrawal force. Also, rotation of the drill bit in the collet is restricted in angular extent by the collet wall so that the drill bit can be removed by merely rotating.

To remove the drill bit from the chuck, it is first necessary to loosen sleeve 40. Then, the drill bit is rotated and axially pulled at the same time in order to remove the boss head 26 from the collet internal wall opening 36. Now, the drill bit may be removed from the collet by simply applying an axial withdrawal force.

Although the foregoing has been a description an illustration of a specific embodiment of the invention, various modifications and changes thereto can be made by persons skilled in the appertaining art without departing from the scope and spirit of the invention as defined by the following claims.

What is claimed is:

1. An axially and rotationally restrained drill bit and chuck assembly, comprising:
   a boss affixed to a drive end of a drill bit, said boss including an enlarged head secured to the drill bit drive and via a smaller dimensioned stem;
   said chuck including a collet having an end opening for receiving the drive end of the drill bit therewithin and an internal wall against which the drill bit drive and bottoms during use, said internal wall including an opening dimensioned to receive the boss enlarged head and wall portions for lockingly contacting said boss enlarged head and restraining said boss enlarged head from both axial release from said opening and from rotating in excess of a predetermined maximum angular extent with respect to the collet.

2. An axially and rotationally restrained drill bit and chuck assembly as in claim 1, in which the boss enlarged head is eccentric to the drill bit rotational axis and the collet internal wall opening is eccentrically located a sufficient amount to enable the boss to be received within the wall opening.

3. An axially and rotationally restrained drill bit and chuck assembly as in claim 1, in which there is further provided a threaded sleeve for threaded receipt onto the collet.

4. An axially and rotationally restrained drill bit and chuck assembly as in claim 1, in which the collet includes a further end opening and a flexible drive shaft having an end portion for receipt within said collet further end opening and secured therewithin.

5. A chuck and drill bit assembly for use with
   a flexible drive shaft, comprising:
   a cylindrical head of a first diameter;
   stem means affixed to both the cylindrical head and the drive end of the drill bit such that the drill bit longitudinal centerline and the head cylindrical axis are substantially parallel and eccentric to one another;
   a hollow cylindrical collet having first and second open ends and an internal wall defining a first chamber for receiving an end portion of the drill bit through the first open end and a second chamber for receiving an end portion of the flexible drive shaft through the second open end;
   said collet internal wall including an opening therein of such location and dimensions as to enable receipt of the cylindrical head therethrough, said internal wall thickness adjacent the opening therein being less than the stem dimensions measured from the drill bit drive end to the cylindrical head;
   a shoulder on the collet internal wall facing into the collet second chamber for contacting the flexible shaft and holding it separated from the cylindrical head; and
   a sleeve threaded onto the collet from the drill bit receiving end.

6. A chuck and drill bit assembly as in claim 5, in which the collet is tapered and has slotted walls.

7. A chuck and drill bit assembly as in claim 5, in which the flexible drive shaft end portion within the collet second chamber is staked to the collet.

* * * * *